United States Patent [19]
Smith

[11] Patent Number: 5,986,128
[45] Date of Patent: *Nov. 16, 1999

[54] USE OF MONOSODIUM IMINODIACETIC ACID SOLUTIONS IN THE PREPARATION OF N-PHOSPHONOMETHYLIMINODIACETIC ACID

[75] Inventor: Lowell Richard Smith, Kirkwood, Mo.

[73] Assignee: Monsanto Company, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/742,523

[22] Filed: Nov. 1, 1996

[51] Int. Cl.$^6$ .............................. C07F 9/38; C07C 229/24
[52] U.S. Cl. .............................................. 562/17; 562/571
[58] Field of Search ........................................ 562/17, 571

[56] References Cited

U.S. PATENT DOCUMENTS

| | | | |
|---|---|---|---|
| 2,384,817 | 9/1945 | Chitwood | 260/531 |
| 3,288,846 | 11/1966 | Irani et al. | 260/500 |
| 3,455,675 | 7/1969 | Irani | 71/86 |
| 3,904,668 | 9/1975 | Gaudette . | |
| 3,950,402 | 4/1976 | Franz | 260/502.5 |
| 4,299,978 | 11/1981 | Nakayasu . | |
| 4,724,103 | 2/1988 | Gentilcore | 260/502.5 |
| 4,782,183 | 11/1988 | Goto et al. | 562/526 |
| 5,011,988 | 4/1991 | Thunberg | 562/554 |
| 5,292,936 | 3/1994 | Franczyk | 562/526 |
| 5,312,972 | 5/1994 | Cullen | 562/17 |
| 5,367,112 | 11/1994 | Franczyk | 562/526 |

FOREIGN PATENT DOCUMENTS

| | | | |
|---|---|---|---|
| 0 155 926 | 9/1985 | European Pat. Off. | C07F 9/38 |
| 0 200 106 | 12/1986 | European Pat. Off. | C07C 51/42 |
| 0 427 401 | 5/1991 | European Pat. Off. | C07C 227/38 |
| 0 595 598 | 5/1994 | European Pat. Off. | C07F 9/38 |
| 1 575 469 | 9/1980 | United Kingdom | C07C 99/12 |

OTHER PUBLICATIONS

College Chemistry by Nebergall et al p. 273 1968.
Merck Index 1983 p. 7231.
CA 104:109025 1985 Abs of JP 6007894—Iminodiacetic acid salts.

Primary Examiner—Gary Geist
Assistant Examiner—Jean F Vollano
Attorney, Agent, or Firm—James M. Warner; Monsanto Company; Arnold White & Durkee

[57] ABSTRACT

A method is described for making solution stable salts of iminodiacetic acid (IDA), useful as precursors in the manufacture of N-phosphonomethylglycine. Concentrated dialkali salts of IDA which are insoluble at temperatures below about 55° C., such as the disodium salt (DSIDA) are acidified to monoalkali salts, such as monosodium IDA (MSIDA). The resulting salts are stable in solution, and may conveniently be stored or transported in solution without recourse to dilution, heating, or similar measures.

25 Claims, No Drawings

USE OF MONOSODIUM IMINODIACETIC ACID SOLUTIONS IN THE PREPARATION OF N-PHOSPHONOMETHYLIMINODIACETIC ACID

BACKGROUND OF THE INVENTION

This invention relates to N-phosphonomethylglycine (glyphosate) and more specifically, to a method of making concentrated monosodium iminodiacetic acid solutions for the preparation of N-phosphonomethylglycine.

N-phosphonomethylglycine (glyphosate) is an important broad spectrum herbicide. One conventional precursor to glyphosate is N-phosphonomethyliminodiacetic acid (PMIDA) having the following formula(I):

An early description of the preparation of above compound (I) is disclosed in U.S. Pat. No. 3,288,846 to Irani et al. In such process iminodiacetic acid (IDA) was employed as a starting material, prepared by hydrolysis of iminodiacetonitrile. Several process steps are required for the recovery and purification of IDA. The acid is then phosphonomethylated with phosphorous acid and formaldehyde in the presence of a mineral acid. In one embodiment, the addition of phosphorus trichloride to the aqueous reaction mixture provides, by hydrolysis, sufficient hydrogen chloride to form the hydrochloride salt of IDA while also providing the phosphorous acid for the phosphonomethylation reaction.

An improvement of the Irani et al process is disclosed in U.S. Pat. No. 4,724,103 to Gentlicore. According to this improvement the dialkali metal salt of IDA, preferably the disodium salt (DSIDA), is employed as the starting material. Upon reaction with a strong mineral acid, typically hydrochloric acid, the DSIDA is converted to the acid salt (IDA•HCl) and the alkali metal salt of the strong acid. The acid salt is then phosphonomethylated by reacting the strong acid salt with phosphorous acid and formaldehyde to provide compound (I) and an alkali metal salt. Water and caustic are added to the reaction mixture in an amount sufficient to dissolve the alkali metal salt and compound (I) is separated as a precipitate. This process eliminated numerous steps for the purification and recovery of IDA from the crude hydrolysate of IDAN thus offering a more economical route to (I). For a description of the numerous steps required to separate and purify IDA from the IDAN hydrolysate see British patent 1,575,469. The elimination of much capital equipment and processing steps will be appreciated by a comparison of the processes of Gentlicore and the British patent.

The process of Gentlicore requires that the DSIDA starting material be maintained at elevated temperatures during shipping and storage because this material crystallizes at temperatures below about 55° C. The crystal form is highly insoluble and inconvenient to dissolve in water for use in the process for preparing compound (I). Accordingly, DSIDA must either be used immediately following its production or stored in a diluted form, or heated to maintain solubility. All such alternatives increase cost.

One attempt to avoid the problem associated with the use of DSIDA is disclosed in U.S. Pat. No. 5,312,972 to Cullen. Cullen discloses an alternative process for preparing compound (I) that involves reacting solutions of a dialkali metal salt of IDA with formaldehyde so as to form the dialkali metal salt of hydroxymethyliminodiacetic acid (HMIDA). Such precursor has the potential for increasing loads of by-product N-methyl iminodiacetic acid in the final product. The HMIDA can be subsequently reacted with a phosphorus source such as phosphorous acid to produce compound (I).

Although the above-mentioned methods achieve their intended purposes, they are limited in use. In particular, DSIDA must be diluted or kept hot to maintain solubility of the concentrate during transport or storage. Dilute solutions contain more liquid and are therefore more expensive to ship. In some instances it is impractical or costly to store and ship solutions while heating to a temperature range sufficient to maintain solubility and prevent crystallization. Using formaldehyde as in Cullen to maintain solubility in concentrated disodium iminodiacetic acid solutions is unacceptable for toxicity reasons.

SUMMARY OF THE INVENTION

In accordance with the present invention, there is provided a method of making a concentrated monosodium iminodiacetic acid solution that may conveniently be stored and transported. These advantages of storage and transport may impart economic and commercial viability to the solution made from disodium iminodiacetic acid, as disclosed herein. This alternative method of making glyphosate precursors should require little dilution or heating to prevent precipitation.

According to this invention, a method is provided for making a concentrated aqueous solution of monosodium iminodiacetic acid (MSIDA) from solutions of disodium iminodiacetic acid. This method comprises adding a strong acid to an aqueous solution consisting essentially of disodium iminodiacetic acid. Surprisingly, this results in a stable aqueous solution at ambient temperatures having up to about 29% iminodiacetic acid equivalents. The resulting solution containing MSIDA may then be stored or transported, thereby reaizig further advantages of the invention disclosed herein.

As used herein, the term "stable" means a solution that can be stored and/or shipped without providing a heat source to prevent crystallization.

As used herein, the term "concentrated" means a solution having a concentration of greater than about 25% IDA equivalents by weight.

DETAILED DESCRIPTION OF A PREFERRED EMBODIMENT

Concentrated di alkali salts of IDA which are insoluble at temperatures below about 55° C., such as the disodium salt (DSIDA) are acidified to monoalkali salts, such as monosodium IDA (MSIDA).

According to the method of this invention, a stable, concentrated aqueous monosodium iminodiacetic acid solution is made by adding a strong acid to an aqueous solution of disodium iminodiacetic acid.

Typical strong acids include suilfric acid and hydrochloric acid. Hydrochloric acid is preferred, however, for reasons of economy and compatibility with subsequent processing. Because hydrochloric acid is preferred, the invention will further be described with reference to hydrochloric acid although any other suitable strong acid can be employed in its place.

Moreover, in another embodiment, one equivalent of phosphorus trichloride may be added to three equivalents of an aqueous solution of DSIDA to form a solution of three equivalents of the monosodium salt of iminodiacetic acid and one equivalent of phosphorous acid. This solution can be used to prepare PMIDA either by adding formalin and additional $PCl_3$ to produce $H_3PO_3$ and the HCl needed to catalyze the phosphonomethylation, or by adding appropriate amounts of phosphorous acid, hydrochloric acid and formaldehyde to achieve the desired phosphonomethylation.

According to the principles of this invention, a sufficient amount of strong acid, preferably from about 0.8 to 1.2 mole equivalent of the strong acid per mole of disodium iminodiacetic acid, is added to an aqueous solution containing disodium iminodiacetic acid.

The disodium iminodiacetic acid in aqueous solution may be formed according to methods known in the prior art. Such methods include basic hydrolysis of IDAN or catalytic dehydrogenation of diethanol amine as disclosed in U.S. Pat. Nos. 2,384,817 to Chitwood, 4,782,183 to Goto et.al, 5,292,936 and 5,367,112 both to Francyzk, said patents being hereby incorporated by reference. The resulting aqueous solution is then treated with sufficient strong acid to convert the DSIDA to MSIDA In one example, the strong acid is introduced as hydrogen chloride gas, which may be added to the disodium iminodiacetic acid and heated in a suitable reaction vessel to form a homogeneous solution of monosodium iminodiacetic acid and sodium chloride.

Although the strong acid is preferably introduced as a gas (such as HCl gas), it may also be added in other forms such as aqueous solutions. However, addition of HCl gas (rather than aqueous acid) gives the added benefit of reducing dilution effects. As noted above, other strong acids may be added instead of hydrochloric acid or sulfuric acid. It is to be understood that the term "hydrochloric acid" as used in the claims encompasses hydrogen chloride gas which forms an acid in aqueous media.

The hydrogen chloride gas is preferably fed into the reaction vessel subsurface over a 45 minute period at temperatures ranging between 55° C. and 95° C. However, in conducting the process of this invention, the temperature of reaction is not critical Preferably, the mixture is prevented from boiling, for example, by cooling and then adding an additional amount of HCl to the mixture while a weak vacuum is applied.

The specific manner in which disodium iminodiacetic acid is reacted with the strong acid is not critical and can be accomplished in many ways. For example, the strong acid may be introduced into a reaction vessel containing a heated solution of disodium iminodiacetic acid and then cooled to ambient temperature.

The reaction can be carried out in any kind of vessel which is resistant to strong acids and has appropriate means for heating, cooling and agitation. The ratio of reactants, that is, the disodium iminodiacetic acid solution and hydrochloric acid or other strong acid is not narrowly critical. However, for best results, at least 0.8 mole equivalent, preferably at least 1.0 mole equivalent, of strong acid is introduced for each mole of disodium iminodiacetic acid. In the case of HCl, best results are obtained using 1.0–1.2 moles of hydrochloric acid per mole disodium iminodiacetic acid. Thus, from about 0.8 to about 1.2 mole equivalent of strong acid per mole of DSIDA is employed in the process of this invention.

The time and temperature of reaction are not narrowly critical In one example, the temperature of the instant reaction ranges from 57.4° C. to 93.4° C. for a period of at least 45 minutes. Nor is pressure critical. Thus, the solutions of the present invention can be prepared at atmospheric, sub-atmospheric or super-atmospheric pressure. It is preferred to conduct the present invention at atmospheric pressure for ease of reaction and economics.

The materials produced by the method of this invention are useful in the manufacture of compounds useful as herbicides and plant growth regulators. As illustrated below, the IDA salts may subsequently be reacted with phosphorous acid, hydrochloric acid and formaldehyde to produce N-phosphonomethyliminodiacetic acid. Because use of the present invention gives stable IDA salt solutions, these materials may be conveniently stored in tanks before subsequent processing, or may be transported without providing heating as a means to maintain solubility.

The following examples serve to further illustrate the invention:

EXAMPLE 1

Hot (57.4° C.) disodium iminodiacetic acid solution (1400 g. 42.38%, 593.3 g. DSIDA, 3.3 moles) was charged to a reactor fitted with an agitator, heating mantle, water condenser and gas introduction tube. A strong acid was introduced by adding hydrogen chloride gas. The hydrogen chloride gas was introduced into the reactor subsurface at 57.4° C. The gas was fed into the reactor for approximately 45 minutes at temperatures between 57.4 and 93.4° C. The heating mantle of the reactor was replaced with a water bath and the reaction mixture was cooled to 73° C. An additional amount of HCl was fed to the cooled mixture while a slight vacuum was applied. A total of 139.2 g. (3.8 moles) of HCl was added. The solution was cooled to ambient temperature. It remained homogeneous, with no significantly observable precipitate. The pH was found to be approximately 4. This solution was suitable for on-site storage or transportation to another site for subsequent processing.

EXAMPLE 2

A solution of monosodium iminodiacetic acid (43.4 g., 30.6% IDA, 13.3 g. 0.1 mole IDA) was prepared and 26 g. of it was placed in a glass reactor capable of low pressure reactions. Hydrochloric acid (37.9% HCl, 18.0 g.) and phosphorous acid (9.46 g.) were added and the mixture was heated to 120° C. Formalin (48.8%, $CH_2O$, 8.2 g.) and the rest of the monosodium IDA solution were added over 30 min. The solution was held at 120° C. for 90 min. and cooled. Filtration, cake washing, and drying gave N-phosphonomethyliminodiacetic acid (21.4 g., 97%, 91% yield) and 56.5 g. of filtrate.

EXAMPLE 3

Preparation of Monosodium Salt of Iminodiacetic Acid/ Phosphorous Acid Solution

A 60° C. solution of disodiumiminodiacetic acid (921 g. 40.35%, 371.6 g. DSIDA, 2.1 moles) was charged to a reactor fitted with an agitator, a heating jacket with an auxiliary heater/cooler, and a water condenser and was heated to 90° C. Over a period of ~60 minutes, phosphorus trichloride (97.6 g. 98.5%, 96.1 g. $PCl_3$, 0.7 moles) was added below the surface of the DSIDA solution. During the course of this addition, the reaction warmed and the temperature was maintained <105° C. The reaction mixture was cooled to 95° C. and 1011 g. of a solution containing 2.08 moles of MSIDA, 2.1 moles of NaCl, and 0.7 moles of $H_3PO_3$ was obtained. This solution may be used to prepare N-phosphonomethylirinodiacetic acid.

What is claimed:

1. A method of making a concentrated aqueous solution of monosodium iminodiacetic acid comprising:

a) providing an aqueous solution of disodium iminodiacetic acid comprising greater than about 25% iminodiacetic acid equivalents by weight:

b) adding strong acid at a ratio of from about 0.8 to about 1.2 mole of strong acid per mole of disodium iminodiacetic acid, thereby creating a stable solution of monosodium iminodiacetic acid comprising greater than about 25% iminodiacetic acid equivalents by weight.

2. The method of claim 1 wherein the stable solution of monosodium iminodiacetic acid comprises about 30% iminodiacetic acid equivalents by weight.

3. The method of claim 1 wherein the aqueous solution of disodium iminodiacetic acid comprises about 40% by weight of disodium iminodiacetic acid.

4. The method of claim 1 wherein the aqueous solution of disodium iminodiacetic acid comprises about 42% by weight of disodium iminodiacetic acid.

5. The method of claim 1 wherein the concentrated aqueous solution of monosodium iminodiacetic acid contains between about 25% and about 29% iminodiacetic acid equivalents by weight.

6. The method of claim 1 wherein the strong acid is hydrochloric acid or sulfuric acid.

7. The method of claim 6 wherein the strong acid is hydrochloric acid.

8. The method of claim 7 wherein the strong acid is added as hydrogen chloride gas.

9. The method of claim 1 wherein the source of the strong acid is provided by the reaction of phosphorus trichloride and water.

10. A method for preparing a concentrated aqueous solution of monosodium iminodiacetic acid comprising:
   a) making disodium iminodiacetic acid in an aqueous solution, said solution comprising greater than about 25% iminodiacetic acid equivalents by weight of disodium iminodiacetic acid; and
   b) adding strong acid to said disodium iminodiacetic acid in an amount sufficient to form an aqueous solution of monosodium iminodiacetic acid.

11. The method of claim 10 wherein disodium iminodiacetic acid is made by hydrolyzing iminodiacetonitrile with an alkali metal base.

12. The method of claim 10 wherein disodium iminodiacetic acid is made by catalytic dehydrogenation of diethanolamine.

13. The method of claim 10 wherein the strong acid is hydrochloric acid or sulfuric acid.

14. The method of claim 10 wherein the strong acid is hydrochloric acid.

15. The method of claim 10 wherein the strong acid is added as hydrogen chloride gas.

16. A method for preparing N-phosphonomethyl iminodiacetic acid comprising:
   a) providing disodium iminodiacetic acid solution comprising greater than about 25% iminodiacetic acid equivalents by weight of disodium iminodiacetic acid;
   b) adding strong acid at a ratio of from about 0.8 to about 1.2 mole of strong acid per mole of disodium iminodiacetic acid, thereby creating a stable solution of monosodium iminodiacetic acid comprising greater than about 25% iminodiacetic acid equivalents by weight;
   c) storing said stable solution at a temperature below about 55° C.; and
   d) processing said stable stored solution, said processing comprising reacting said monosodium iminodiacetic acid with additional strong acid, phosphorous acid and formaldehyde.

17. The method of claim 16 wherein said additional strong acid and phosphorous acid are provided by adding phosphorus trichloride to said stable stored solution.

18. The method of claim 16 wherein the stable solution is stored at ambient temperature.

19. A method for preparing N-phosphonometlyliminodiaiceticacid comprising:
   a) providing disodium iminodiacetic acid solution comprising greater than about 25% iminodiacetic acid equiquivalents by weight of disodium iminodiacetic acid;
   b) adding strong acid at a ratio of from about 0.8 to about 1.2 mole of strong acid per mole of disodium iminodiacetic acid, thereby creating a stable solution of monosodium iminodiacetic acid comprising greater than about 25% iminodiacetic acid equivalents by weight;
   c) transporting said stable solution to another location; and
   d) processing said stable transported solution, said processing comprising reacting said monosodium iminodiacetic acid with additional strong acid, phosphorous acid, and formaldehyde.

20. The method of claim 19 wherein said additional strong acid and phosphorous acid is provided by adding phosphorus trichloride to said stable solution.

21. A stable solution comprising monosodium iminodiacetic acid at a concentration greater than about 25% equivalent iminodiacetic acid and a temperature below about 55° C.

22. The stable solution of claim 20 wherein the monosodium iminodiacetic acid concentration is greater than about 29% equivalent iminodiacetic acid.

23. The stable solution of claim 20 wherein the monosodium iminodiacetic acid concentration is up to about 29% iminodiacetic acid equivalents by weight, and wherein the temperature of the stable solution is ambient temperature.

24. A method of making a concentrated aqueous solution of monosodium iminodiacetic acid comprising:
   a) providing an aqueous solution of disodium iminodiacetic acid comprising greater than about 25% iminodiacetic acid equivalents by weight;
   b) adding strong acid at a ratio of from about 0.8 to about 1.2 mole of strong acid per mole of disodium iminodiacetic acid, thereby creating a stable solution of monosodium iminodiacetic acid comprising greater than about 25% iminodiacetic acid equivalents by weight;
   c) cooling the stable solution of monosodium iminodiacetic acid to ambient temperature.

25. The process of claim 23 wherein the temperature of the solution during the addition of strong acid is maintained at between about 55° to about 95° C.

* * * * *

UNITED STATES PATENT AND TRADEMARK OFFICE
CERTIFICATE OF CORRECTION

PATENT NO.    : 5,986,128
DATED         : November 16, 1999
INVENTOR(S)   : Lowell Richard Smith It is certified that error appears in the above-identified patent and that said Letters Patent is hereby corrected as shown below:

In claim 16, column 5, lines 50-51, delete "N-phosphonomethyl iminodiacetic" and insert therefor --N-phosphonomethyliminodiacetic--.

In claim 16, column 5, line 63, delete "C.;" and insert therefor --C;--.

In claim 22, column 6, line 37, delete "20" and insert therefor --21--.

In claim 23, column 6, line 40, delete "20" and insert therefor --21--.

In claim 25, column 6, line 59, delete "23" and insert therefor --24--.

Signed and Sealed this

Nineteenth Day of September, 2000

Attest:

Q. TODD DICKINSON

*Attesting Officer*   *Director of Patents and Trademarks*